United States Patent [19]
Manz

[11] Patent Number: 5,595,650
[45] Date of Patent: Jan. 21, 1997

[54] DEVICE AND A METHOD FOR THE SEPARATION OF FLUID SUBSTANCES

[75] Inventor: Andreas Manz, Bettingen, Switzerland

[73] Assignee: Ciba-Geigy Corporation, Tarrytown, N.Y.

[21] Appl. No.: 396,045

[22] Filed: Feb. 28, 1995

[30] Foreign Application Priority Data

Mar. 3, 1994 [CH] Switzerland ................ 633/94

[51] Int. Cl.$^6$ ................................................. B01D 15/08
[52] U.S. Cl. ................................ 210/198.2; 210/657
[58] Field of Search ................................ 210/635, 657, 210/656, 658, 659, 198.2, 198.3

[56] References Cited

U.S. PATENT DOCUMENTS

| | | | |
|---|---|---|---|
| 3,732,982 | 5/1973 | Dunnill | 210/657 |
| 3,775,309 | 11/1973 | Ito | 210/657 |
| 4,353,795 | 10/1982 | Romanauskas | 209/155 |
| 4,356,083 | 10/1982 | Romanauskas | 209/155 |
| 4,357,235 | 11/1982 | Dilks | 209/1 |
| 4,857,187 | 8/1989 | Ito | 210/657 |
| 4,908,112 | 3/1990 | Pace | 210/198.2 |
| 5,116,495 | 5/1992 | Prohaska | 210/198.2 |
| 5,132,012 | 7/1992 | Miura | 210/198.2 |
| 5,296,114 | 3/1994 | Manz | 204/180.1 |

FOREIGN PATENT DOCUMENTS

| | | | |
|---|---|---|---|
| 0544969 | 6/1993 | European Pat. Off. | 204/180.1 |

OTHER PUBLICATIONS

L. R. Snyder and J. J. Kirkland, Introduction to Modern Liquid Chromatography, 2nd Edition, John Wiley & Sons (1979) pp. xiii–xix.

G. Fuhr and B. Wagner, Surface–charge Induction Micromotors With Two Aluminium Rotors isolated By $SiO_2$, The 7th International Conference on Solid State Sensors and Actuators pp. 88–92.

G. Fuhr et al., Sensors and Actuators vol. A32 No. 1–3 Apr. 1992 pp. 525–530.

*Primary Examiner*—Ernest G. Therkorn
*Attorney, Agent, or Firm*—George R. Dohmann

[57] ABSTRACT

A device for the separation of fluid substances, especially a capillary chromatographic separating device, is provided, which comprises a separating path in which a stationary phase is arranged and through which flows a mobile phase containing a sample to be separated into its components. The device also comprises means for transporting the mobile phase, and a detection device for detecting the separated components. The separating path is constructed in the form of an annular channel into which lead the inflow and outflow channels for the mobile phase and the fluid substance to be separated. In a very especially preferred variant of the invention the means for transporting the mobile phase are arranged inside the annular channel. In the described method of separating fluid substances the mobile phase together with the sample to be separated is circulated cyclically in a separating path constructed in the form of an annular channel. The circulation is preferably effected with the aid of transport means arranged inside the annular channel.

13 Claims, 8 Drawing Sheets

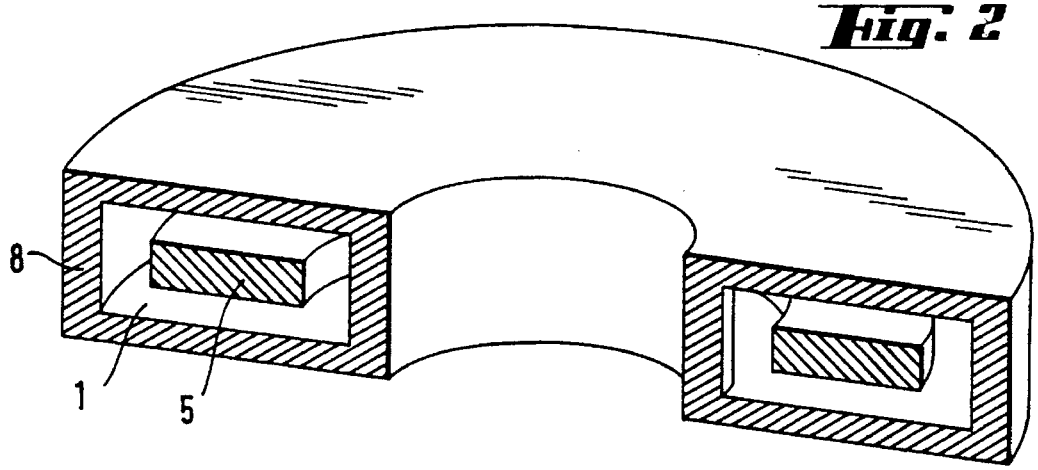
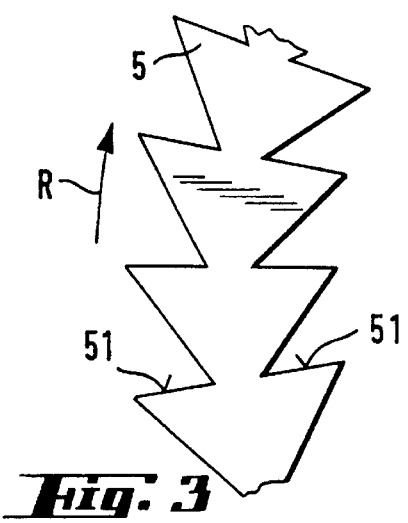
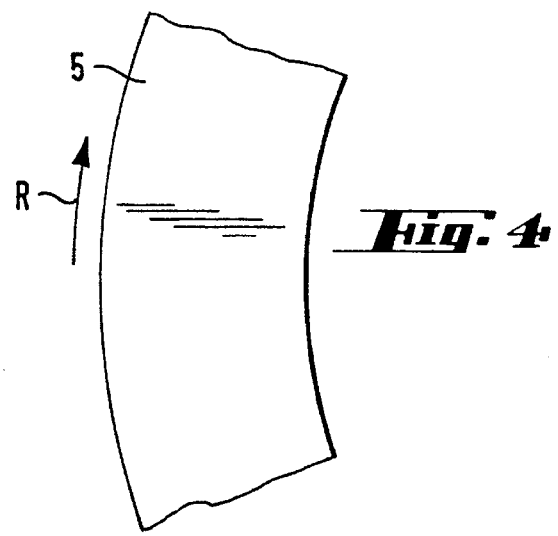
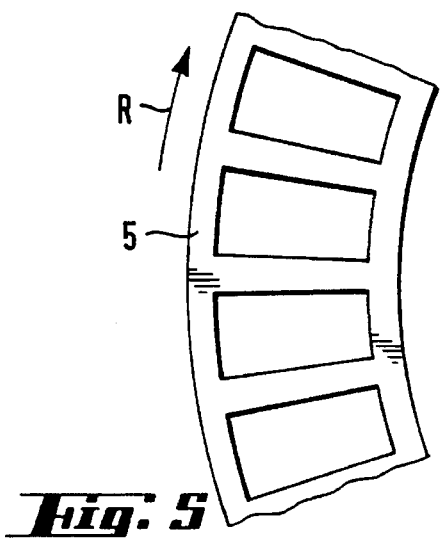
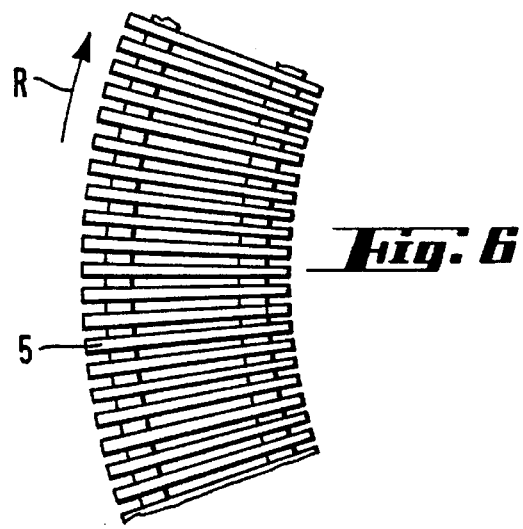

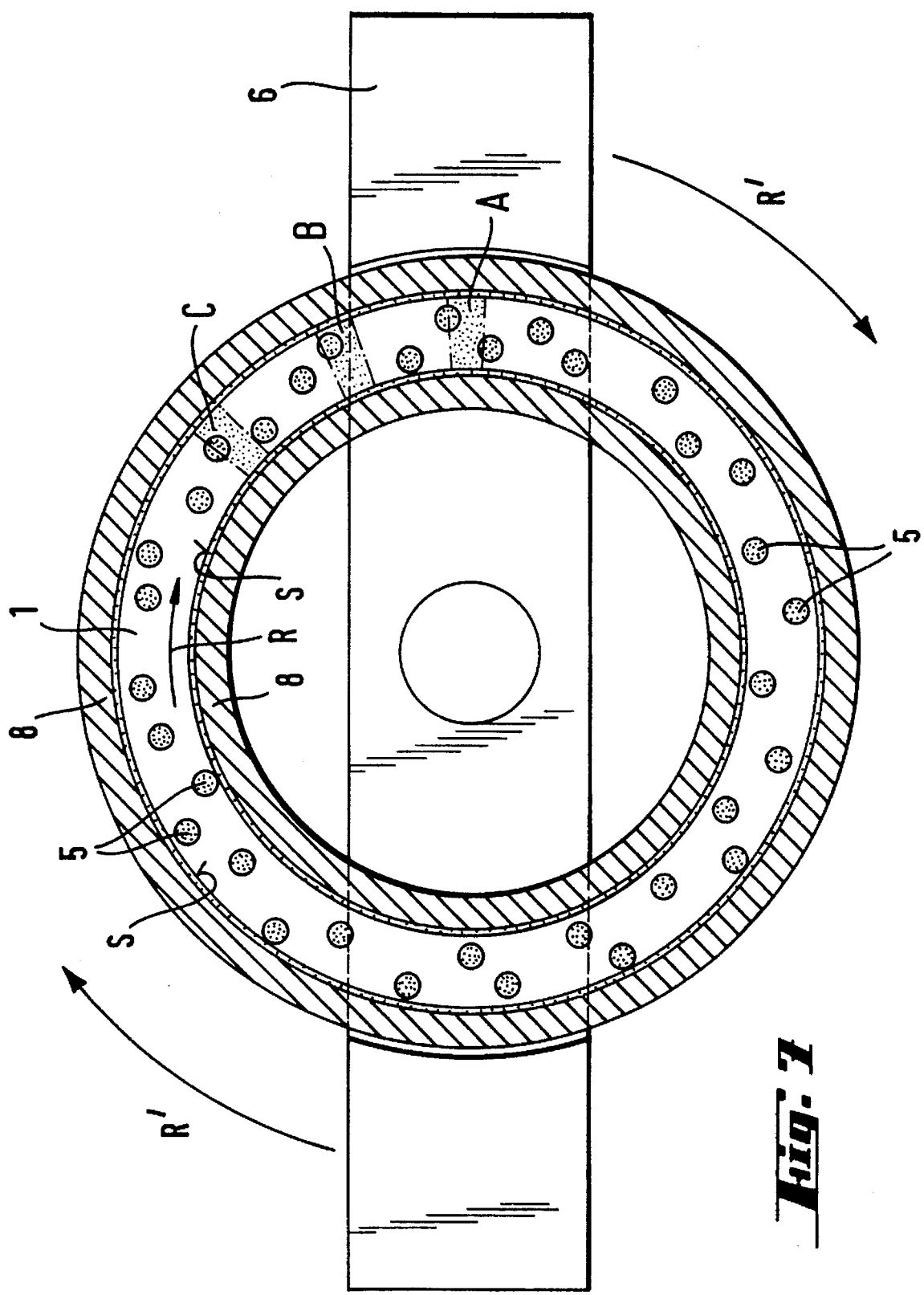

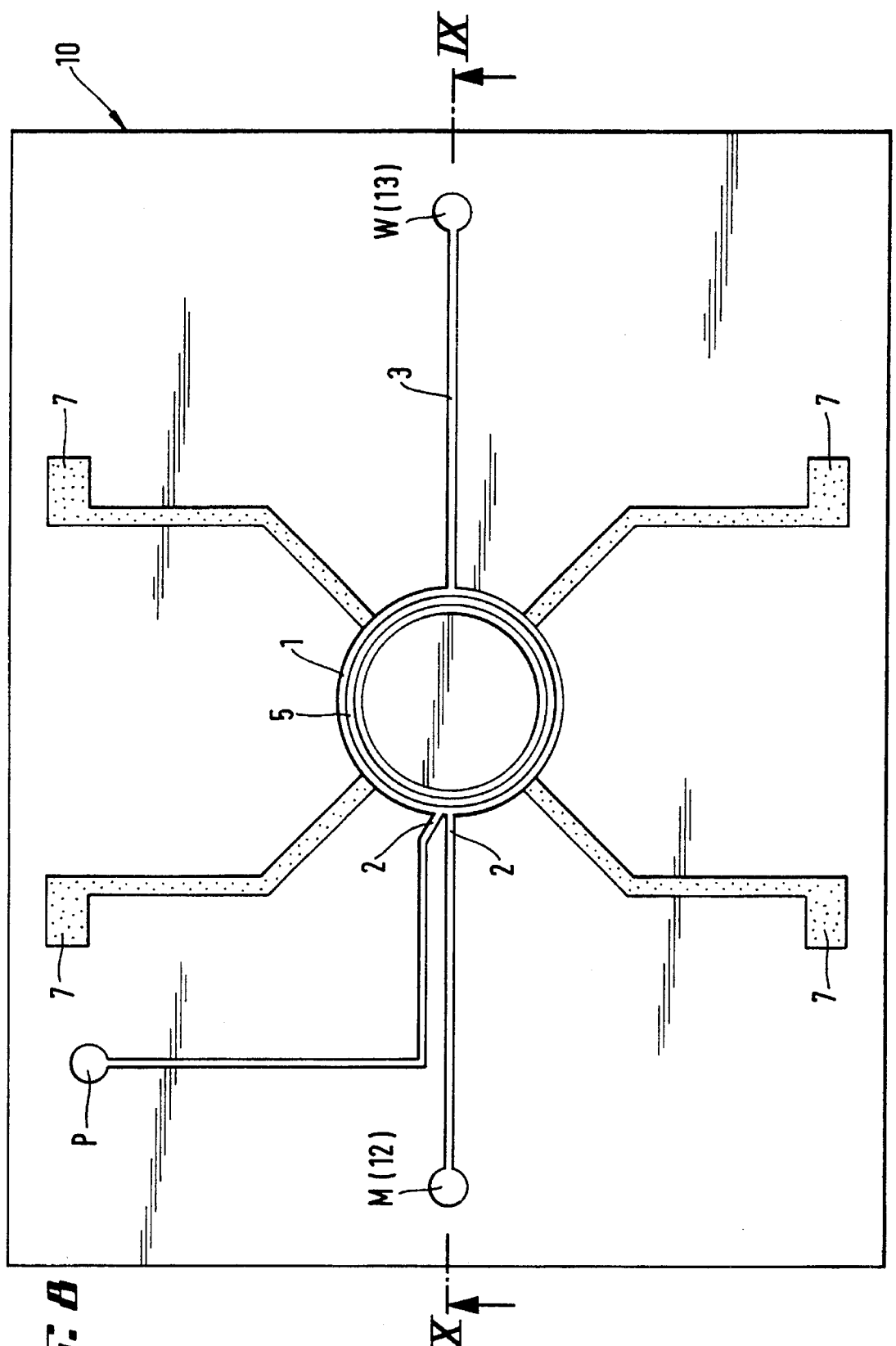

DEVICE AND A METHOD FOR THE SEPARATION OF FLUID SUBSTANCES

The invention relates to a device and a method for the separation of fluid substances, especially to a device and a method for capillary liquid chromatography, in accordance with the preamble of patent claim 1 and in accordance with the preamble of patent claim 13, respectively.

Liquid chromatography, and especially High Performance Liquid Chromatography (HPLC), is an established technique for the preparative or analytical separation of fluid substances into their individual components. Chromatographic separation is based on the migration of a mobile phase through a stationary phase, the components to be separated being transported at different speeds. In the stationary phase, which is usually arranged in a chromatography column, the components to be separated become differentially dispersed in the mobile phase. This continual differential dispersion brings about a continuous separating process.

In modern liquid-chromatographic separating methods the stationary phase is generally arranged inside a glass column or a steel column, through which the mobile phase flows. In order to increase the separating efficiency a pressure gradient of 200–300 bar is often established in the separating column (HPLC). Liquid chromatography and especially HPLC are very flexible separating methods which can be used flexibly and which have become well established and generally accepted. Disadvantages of liquid chromatography and especially of HPLC are the modest separating performances that are obtained despite the relatively high level of technical resources used (for example special high pressure valves in HPLC), and the long analysis times of 20–40 minutes with a cycle time of 30–60 minutes. Typical flow rates for the mobile phase are about 2–5 ml/min. In addition, such conventional chromatographic separating techniques require large amounts of reagents, which in many cases is undesirable and limits their scope for use in the separation and analysis of small sample volumes.

In the known capillary liquid chromatography, thin capillaries having internal diameters of only 1–5 μm are used. Although that separating technique is theoretically very efficient and should produce a good separating performance in a relatively short time, its use requires a high degree of specialist knowledge and places great demands on the equipment and on the skill of the user. System pressures of 200–300 bar are necessary for the operation of such operating systems, but no known pumps are capable of conveying picolitres or nanolitres per minute at such pressures or of maintaining the high pressures in the system with the small amounts being conveyed. A further problem is presented by the injection and the detection of extremely small volumes of, for example, only 1 pl.

An alternative separating technique for the separation of fluid substances into their components is electrophoresis. In that separating technique, molecularly dispersed or colloidally dispersed particles migrate at different rates in an electric field and are thus separated. EP-A-0 544 969 (corresponding to U.S. Pat. application Ser. No. 07/983 178) describes a device in which a substance to be separated is transported cyclically along a closed path and in the process is separated electrophoretically in an electric field that can be applied segment by segment. Using that device, which is preferably miniaturised, it is possible to obtain very high separating performances which become even higher as the separating time increases. The voltage changeover from segment to segment must be timed very accurately in order that the component to be analysed remains in the detectable "window" and is not lost as components circulating too quickly or too slowly are.

The problem underlying the present invention is therefore to provide a device and a method for the separation of fluid substances which eliminate the disadvantages and difficulties of the relevant prior art. In so doing the advantages of the chromatographic separating technique should be utilised and the application of electric separating fields, which may also have to be synchronised, should be unnecessary. In particular, a capillary chromatographic separating method and an associated device are to be provided that are very efficient and that enable a high separating performance to be obtained but at the same time allow rapid separation and analysis. The method and the device should also be suitable for very small sample volumes; it should be possible to dispense with the very high pressures of 200–300 bar necessary for capillary chromatography. The device should also make it possible to broaden the principle of using a stationary phase and a mobile phase on which chromatographic separating techniques are based. The device should be easy to miniaturise and should be be capable of being manufactured at relatively low cost using mass production techniques.

All those problems and other, inherent problems are solved by a device and a method for the separation of fluid substances in accordance with the characterising part of the respective independent patent claims 1 and 13.

The invention provides especially a device for the separation of fluid substances, especially a capillary chromatographic separating device, which comprises a separating path in which a stationary phase is arranged and through which flows a mobile phase containing a sample to be separated into its components. The device also comprises means for transporting the mobile phase and a detection device for detecting the separated components. The separating path is constructed in the form of an annular channel into which lead inflow and outflow channels for the mobile phase and the fluid substance to be separated. As a result of the annular construction of the separating path the overall length of the device can be appreciably reduced. An injected sample undergoes separation in the course of its periodic circulation in the annular channel in which the stationary phase is arranged. The pressure build-up takes place in the annular channel; external very high pressure devices are unnecessary. In this way, for example, separation at 300 bar in a 1 metre long capillary of 3 μm diameter can be replaced by the use of a device having an annular channel of the same diameter and having a circumference of 1 cm in which the sample completes 100 circuits.

In an especially preferred variant of the invention the means for transporting the mobile phase are arranged inside the annular channel. It is thus possible to dispense with external pumps for the cyclic circulation of the mobile phase, containing the sample to be separated, in the annular channel. The separation takes place as it were inside the pump. In a method for the separation of fluid substances, especially in a capillary chromatographic separating method, a sample to be separated into its components is injected into a mobile phase and transported together with the mobile phase through a separating path in which a stationary phase is arranged. In that process the sample is separated into its components as a result of its interaction with the stationary phase, and the components can then be detected using a detection device. According to the invention the mobile phase together with the sample to be separated is circulated cyclically in a separating path constructed in the form of an annular channel.

In an especially preferred process variant the mobile phase and the sample to be separated are circulated cyclically using means that are arranged inside the annular channel. In this way the annular channel with the transport means arranged therein is itself utilised as a pressure-building conveying device.

Other especially preferred variants of the invention are to be found in the respective dependent patent claims. The invention, with all its associated details essential to the invention, is described in greater detail below by way of examples of variants shown in diagrammatic form.

BRIEF DESCRIPTION OF THE DRAWINGS

FIG. 2 shows a segment of the annular separating channel with the rotor arranged therein, FIG. 3–6 show examples of rotor shapes, FIG. 7 shows an annular separating channel with the rotor arranged therein divided into particle form and with drive means for the rotor, FIG. 8 is a plan view of a chip variant of the invention, FIG. 9 is an axial section through the chip variant of the invention, FIG. 10a,b show the speed profile in a mobile phase circulating cyclically in the annular separating channel.

DESCRIPTION OF THE PREFERRED EMBODIMENTS

Figure 1:
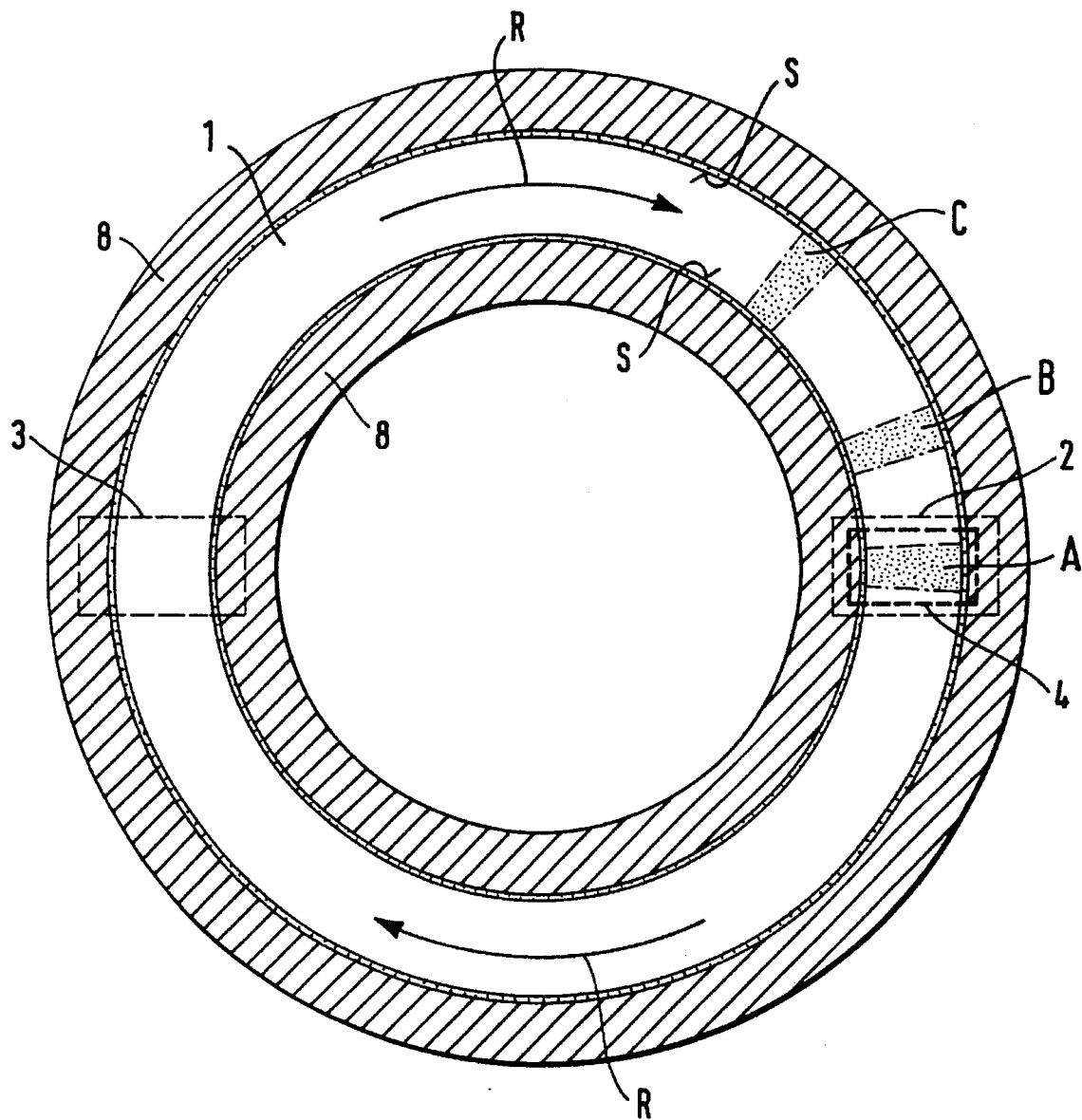
FIG. 1 is a diagram illustrating the principle of the device according to the invention with the annular separating channel.

FIG. 1 shows the components of the invention relevant to the invention. In particular, FIG. 1 shows a capillary-form separating path 1 in which a stationary phase S is arranged. The separating path 1 is constructed in the form of an annular channel into which lead inflow and outflow channels 2 and 3 for a mobile phase and a sample to be separated. In FIG. 1 an inflow channel 2 and an outflow channel 3 are each indicated by dashed-line boxes. In the embodiment of the device shown, the stationary phase S is arranged on the boundary wall 8 of the annular separating channel 1. An overview of the different materials that can be used as stationary phases and of the principles of their mechanisms of interaction with various types of sample is given, for example, in "L. R. Snyder and J. J. Kirkland, Introduction to modern liquid chromatography, Second Edition, John Wiley & Sons, U.S.A. 1979". Transport means (not shown) for the mobile phase and for the sample injected into the mobile phase ensure that the mobile phase and the sample are circulated cyclically in the separating channel 1, as indicated by arrow R. The transport means may be, for example, pumps that are arranged in the inflow and outflow channels. During its cyclic circulation in the annular separating channel 1 the sample interacts with the stationary phase S and is separated into its components, for example into components A, B and C as shown. Components A, B and C have different circulation speeds in the annular separating channel and are therefore separated further with every circuit. A detection device 4, for example an optical detection system for absorption or fluorescence measurements, is arranged along the annular separating channel 1. It is preferably arranged, as shown, in the region of the point of entry of the inflow channel 2, since in that way a component flowing through is always detected only after it has completed a full circuit. It will be understood that the detection device 4 also comprises evaluating devices (not shown) in which the detected signals are further processed. In the diagram shown illustrating the principle, it is, for example, component A that is at this instant located in the detection window, or detection volume, of the detection device 4.

As a result of the annular construction of the separating path 1 the overall length of the device can be appreciably reduced. The separation of an injected sample takes place during its periodic circulation in the annular separating channel 1 in which the stationary phase S is arranged. The pressure build-up takes place in the annular separating channel 1 itself; external very high pressure devices are unnecessary. In this way, tier example, separation at 300 bar in a 1 metre long capillary of 3 μm diameter can be replaced by the use of a device having an annular channel of the same diameter and having a circumference of 1 cm in which the sample completes 100 circuits. The separating performances obtainable in this way are in the order of up to 400 000 theoretical separating steps. The separating times required with the separating device according to the invention are significantly shorter than those required with known separating devices and are typically about 30 seconds.

A very especially preferred variant of the invention is shown in cut-open view in FIG. 2. In this variant the transport means for the mobile phase and the injected sample are arranged inside the annular separating channel 1. In the embodiment shown the transport means are formed by a toroidal, flat-ring-shaped rotor 5 which can rotate freely inside the annular channel 1. The rotational movement of the rotor 5 is transferred to the surrounding mobile phase containing the sample to be separated. It is thus possible to dispense with external pumps for cyclically circulating the mobile phase containing the sample to be separated in the annular separating channel 1. The separation takes place as it were inside the pump.

Figure 4:
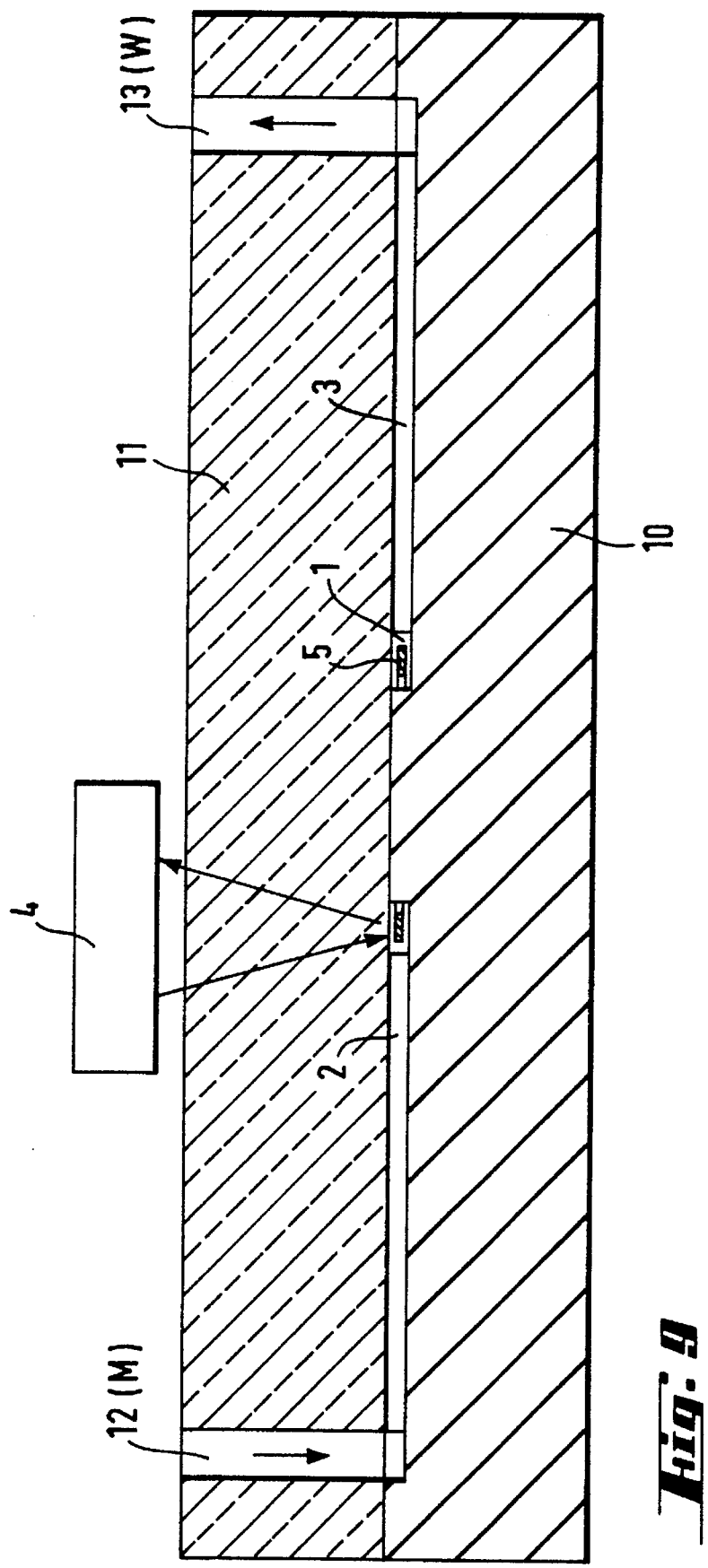

FIGS. 3–6 shows some examples of rotor shapes. The most general shape of the rotor 5 is shown in FIG. 4. The rotor 5 in this case is very similar to an O-ring of rectangular cross-section. Alternative rotor shapes are shown in FIGS. 3, 5 and 6. The rotor 5 in FIG. 3 has sawtooth-like notches along its inner and outer circumference. The direction of rotation of a rotor of that shape is so selected that it is the radial surfaces 5 1, being the surfaces offering the greatest resistance, that propel the mobile phase. The rotors 5 shown by way of example in FIGS. 5 and 6 are in the form of ladders having differently sized spacings between the rungs. The cross-section of all the rotors 5 is generally rectangular.

A feature common to all the rotors 5 shown in FIGS. 3, 5 and 6 is that their shape allows the mobile phase to intermix with the sample vertically with respect to the circumference of the rotor 5 in the annular separating channel 1. This can prevent the mobile phase from forming into a layer above the rotor 5 and a layer below the rotor 5, which might impair the separation.

FIG. 7 shows a separating device having a further variant of the rotor 5 inside the annular separating channel 1. In this case the rotor 5 is divided into small particles which as a result of impact processes transfer momentum to the mobile phase and to the sample and cause them to circulate cyclically in the annular separating channel 1. A rotor 5 that is divided into particles will have virtually no impeding effect on the intermixing of the mobile phase inside the annular separating channel 1.

The rotor 5 is made of metal or is partially metallised, is preferably magnetic and can be driven inductively by drive means 6 that are preferably arranged outside the annular separating channel 1. In the embodiment according to FIG. 7, those drive means 6 are formed by a rotatable permanent magnet in the manner of a magnetic stirrer. The rotation R' of the permanent magnet 6 results in a corresponding cyclic circulation of the particle-form rotor 5. The individual particles transfer momentum to the mobile phase containing the sample and bring about the cyclic circulation thereof inside the annular separating channel in accordance with arrow R. The rotational speed of the permanent magnet 6 is preferably adjustable in accordance with the requirements.

In the embodiment of the device according to the invention shown in FIG. 8 the rotor 5 can be driven by a rotating electric field. The rotational speed of the rotating field is adjustable in accordance with the requirements. In this embodiment the annular channel 1 with inflow and outflow channels 2 and 3 is made using the planar technique on a plate of glass, polymer or monocrystalline material. The inflow and outflow channels 2 and 3 are connected to reservoirs for the mobile phase M, the sample P and the mixture thereof W. When the device is realised using the planar technique and using micromechanical and/or microelectronic manufacturing techniques on plates of glass, polymer or monocrystalline material, it is also possible for any electrical contacts 7 to be integrated on the chip. The manufacturing process for the miniaturised rotor 5 is described, for example, in "G. Fuhr, B. Wagner, Transducers '93 Digest of Technical Papers", ed. Institute of Electrical Engineers of Japan, Tokyo 1993 (ISBN 4-9900247-2-9), pages 88–92.

FIG. 9 shows a section through the device along the line connecting M and W in FIG. 8. The device comprises a base part 10 in which the trough-like inflow and outflow channels 2 and 3 and the annular separating channel 1 with the rotor 5 contained therein are made, and a preferably transparent lid part 11 having attachment openings 12 and 13 for the inflow and outflow capillaries 2 and 3. The transparency of the lid part 11 enables optical measurements to be made through the lid part 11, as indicated by the arrows near the device 4. The measurement takes place along the annular separating channel 1, preferably in the region of the point of entry of the inflow channel 2.

The annular separating channel 1 is constructed in the manner of a capillary. The dimensions of the separating channel corespond to a capillary diameter of from approximately 0.1 μm to approximately 100 μm, preferably approximately 2–5 μm. The circumference of the annular separating channel is from approximately 50 μm to approximately 10 cm. The dimensions of the inflow and outflow channels 2 and 3 correspond largely to those of the annular separating channel 1. This simplifies the manufacturing process and prevents undesirable pressure gradients.

Figure 10A:
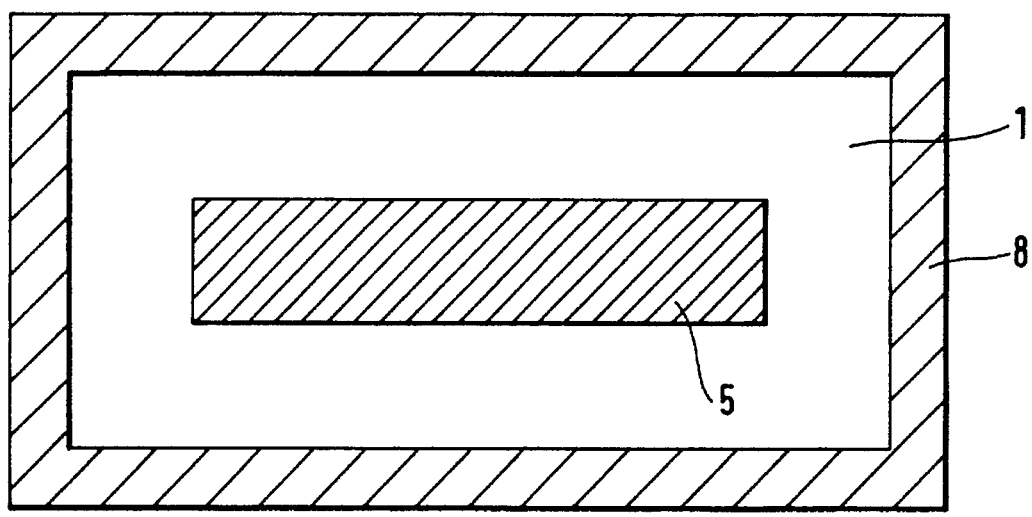
Figure 10B:
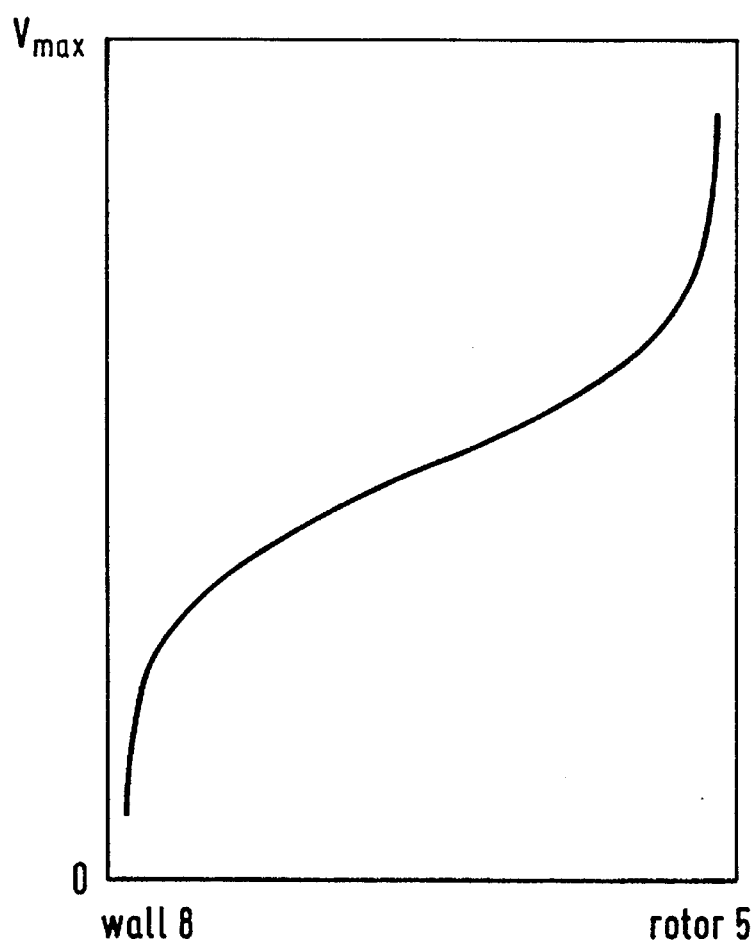

FIGS. 10a and 10b serve to illustrate the speed profile in the mobile phase between the revolving rotor 5 and the boundary wall 8 of the annular channel 1. The speed of the mobile phase is at its minimum at the stationary boundary wall 8. The speed increases in the direction towards the revolving rotor 5 until it reaches its maximum directly at the rotor.

Figure 11:
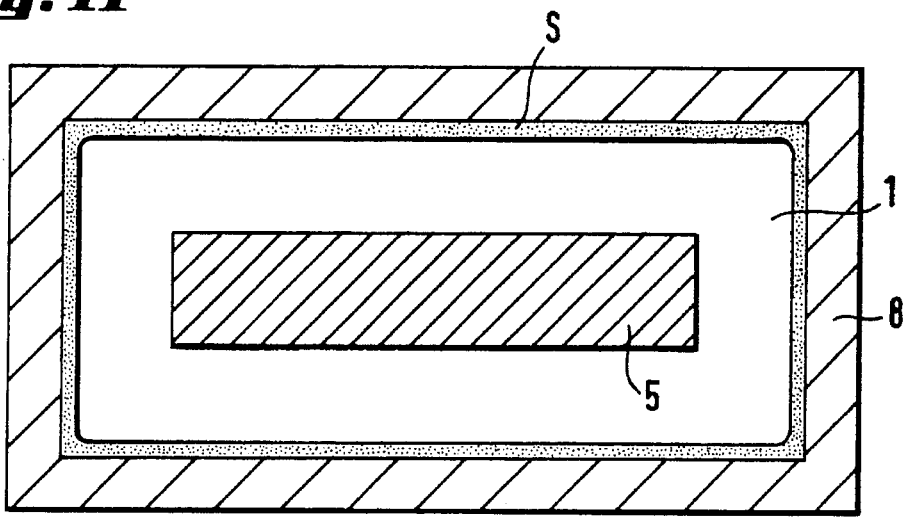
FIG. 11–13 show different variants of the arrangement of a stationary phase inside the annular separating channel.
Figure 12:
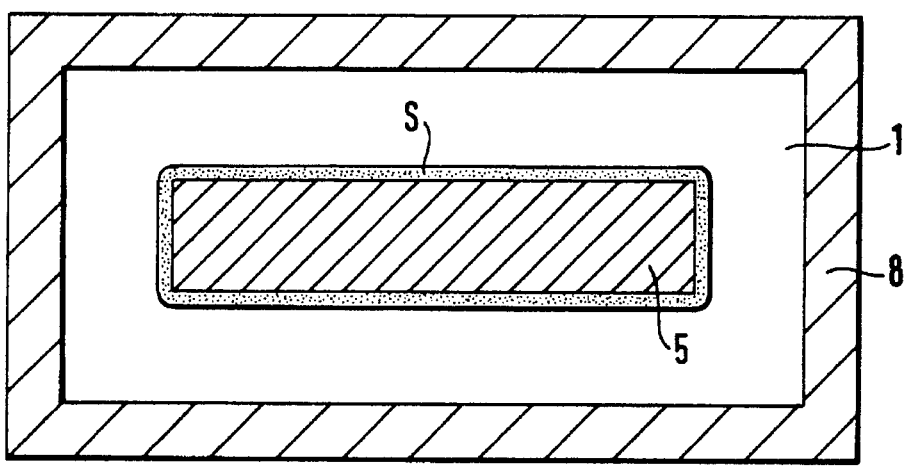
Figure 13:
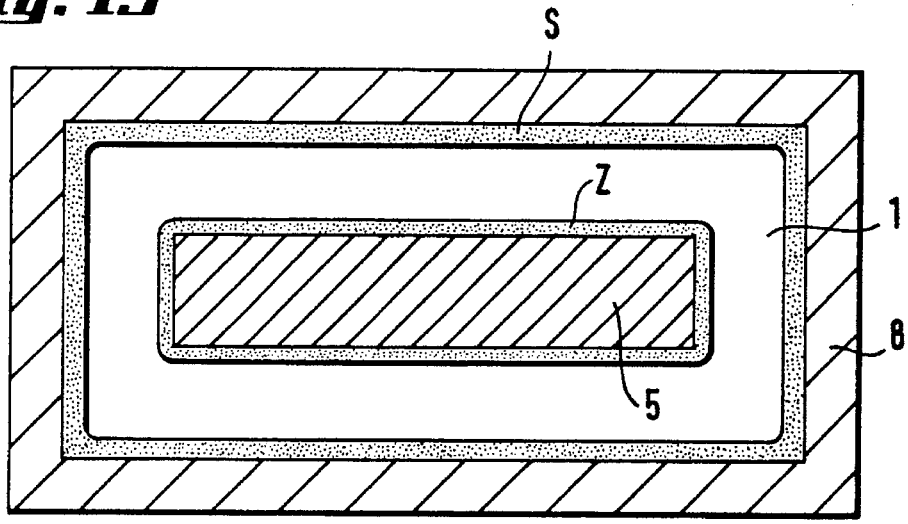

A special advantage of the arrangement of the drive means 5 for the mobile phase and the sample inside the annular separating channel 1 is also that the stationary phase can be arranged as desired on the boundary wall 8 of the separating channel 1 or on the rotor 5 or on both. This is shown in FIGS. 11 to 13. In addition, this preferred variant of the invention allows two different stationary phases S and Z to be used. One of the stationary phases, for example phase S, is arranged on the boundary wall of the annular separating channel 1, as shown in FIG. 13, while the second stationary phase Z is arranged on the rotor. In this way even more selective separation can be carried out, which again increases the separating performance. For example, the first stationary phase S, which is arranged on the boundary wall 8 of the separating channel 1, is very hydrophilic. The second stationary phase Z is arranged on the rotor 5 and, in contrast, is, for example, very lipophilic. The mobile phase is a medium of moderate lipophilicity and hydrophilicity. The lipophilic components of the sample move with the greatest speeds in the separating channel 1. The maximum speed is up to twice the speed of the circulating mobile phase. The hydrophilic components, however, have the lowest circulation speeds. It is thus possible to achieve excellent selective separation even of very rapidly circulating components.

Figure 14:
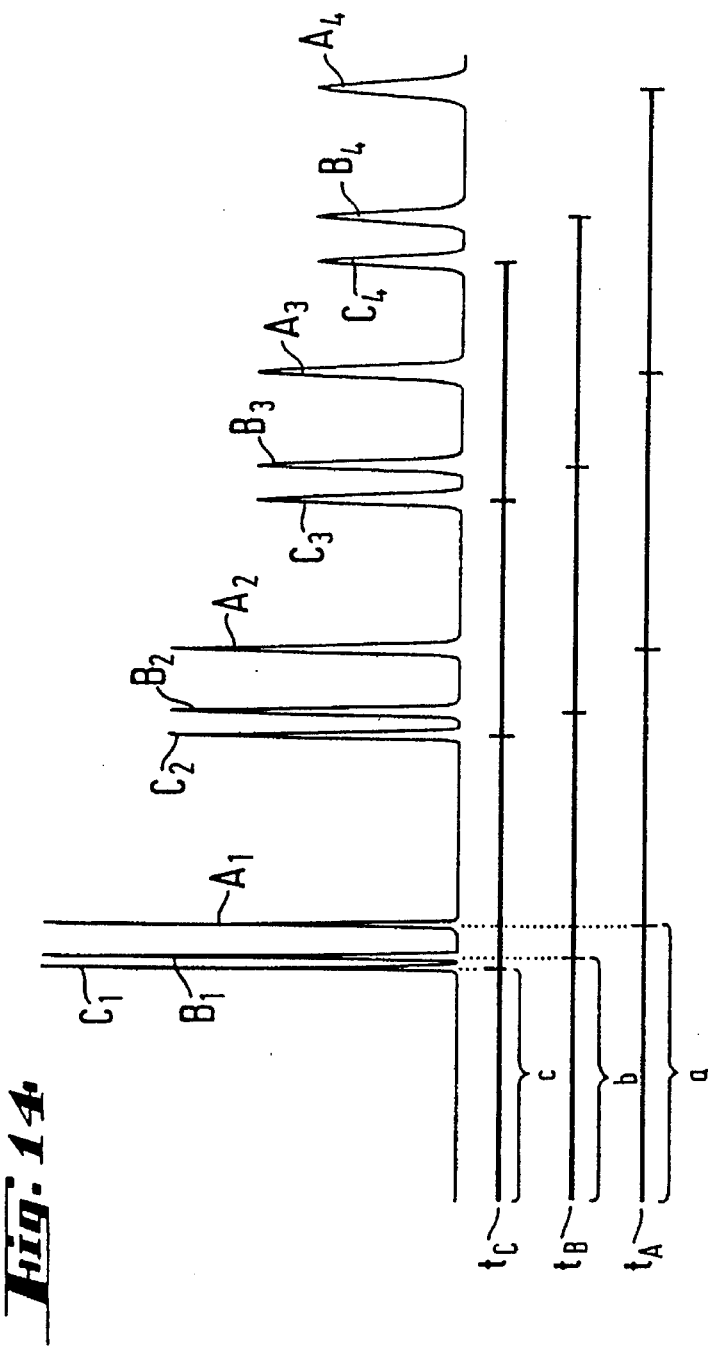
FIG. 14 shows an example of signals registered by a detector device during the circuits.
Figure 15:
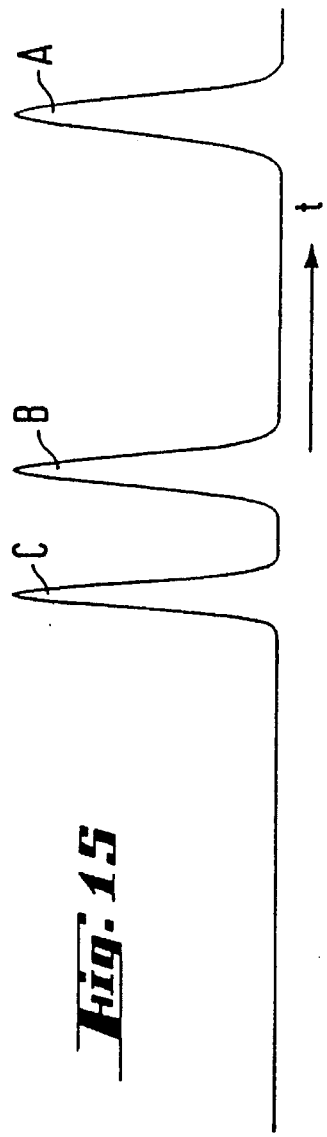
FIG. 15 shows a chromatogram obtainable by transformation of the detected signals.

As a result of the different circulation periods of the individual components of the separated sample, it is possible that individual components may overtake one another. FIG. 14 shows the continuous increase in distance between the individual components for four circuits. The peaks A, B, C with the corresponding indices represent the signals detected by the detection device on each completed circuit. The time scales $t_A$, $t_B$, $t_C$ for components A, B and C are given below the peaks. The circulation periods of the individual components are indicated by a, b and c. By referring to this simplified illustration of an example it can easily be seen that after a certain number of circuits component A will overtake first component C and then component B. Analogously, after a certain higher number of circuits component B will also overtake component C. These overtaking events recur periodically. In order, therefore, to interpret the resulting signal diagram it is necessary to transform the data. This is done by using an orthogonal transformation, especially a suitable Fourier transformation, which provides the associated frequency spectrum. By applying this transformation it is possible to recombine the detected peaks and organise them in an unambiguous manner. The resulting graph has the form of the chromatograms usually obtained and can be evaluated further in the customary form (FIG. 15).

The device according to the invention and the method according to the invention eliminate the disadvantages of known chromatographic techniques. The efficiency of capillary chromatography is utilised without the need to tolerate the disadvantage of high pressures and the limitations imposed by the conventional pump systems available. The special variant of the device with a revolving rotor arranged inside the annular separating channel allows the chromatographic principle to be broadened with the effect that it is now possible to use two different stationary phases for the separation in order further to increase the selectivity of the chromatographic separation. The device is easy to miniaturise and to produce using micromechanical and/or microelectronic manufacturing techniques. It even allows electrical and electronic elements to be integrated directly on the device it is when manufactured using the planar technique.

What is claimed is:

1. A device for the separation of fluid substances, especially a capillary chromatographic separating device, which comprises a separating path in which a stationary phase is arranged and through which a mobile phase and an injected sample to be separated into its components flow, and means for transporting the mobile phase, and a detection device for detecting the separated components, wherein the separating path is constructed in the form of an annular channel into which lead the inflow and outflow channels for the mobile phase and the fluid substance to be separated, wherein the means for transporting the mobile phase together with the injected sample are arranged inside the annular channel.

2. A device according to claim 1, wherein the device is adapted for use as a capillary chromatographic separating device.

3. A device according to claim 1, wherein the means for transporting the mobile phase and the sample are formed by a rotor that has a toroidal or a flat-ting shape or that is divided into particles, which rotor can be rotated freely inside the annular channel.

4. A device according to claim 3, wherein the rotatable rotor is constructed in such a manner that the mobile phase and the sample are able to intermix in the vertical direction of the annular channel largely freely.

5. A device according to claim 4, wherein the rotor is metallic or is partially metallised.

6. A device according to claim 5, wherein the drive means are a rotating permanent magnet or a rotating electric or magnetic field the rotational speeds of which are variably adjustable.

7. A device according to claim 5, wherein the rotor is magnetic and is driven inductively.

8. A device according to claim 1, wherein the detection device is arranged along the annular channel.

9. A device according claim 1, wherein the annular channel is constructed in the manner of a capillary and has a capillary diameter of from approximately 0.1 µm to approximately 100 µm.

10. A device according to claim 1, wherein the annular channel with inflow and outflow channels, and the means for transporting the mobile phase with the injected sample and are arranged using the planar technique on a plate of glass, polymer or monocrystalline material.

11. A device according to claim 1, wherein the circumference of the annular channel is from approximately 50 µm to approximately 10 cm.

12. A device according to 1, wherein the stationary phase is arranged on the inner wall of the channel and/or on the means for transporting the mobile phase together with the injected sample.

13. A device according to claim 1, wherein two different stationary phases are arranged inside the annular channel, one of the two stationary phases being arranged on the inner wall of the channel and the other stationary phase being arranged on the means for transporting the mobile phase and the sample.

* * * * *